(12) United States Patent
Burkholz et al.

(10) Patent No.: US 10,232,088 B2
(45) Date of Patent: Mar. 19, 2019

(54) ANTIMICROBIAL COATING FORMING KINK RESISTANT FEATURE ON A VASCULAR ACCESS DEVICE

(71) Applicant: Becton, Dickinson and Company, Franklin Lakes, NJ (US)

(72) Inventors: Jonathan Karl Burkholz, Salt Lake City, UT (US); Siddarth K. Shevgoor, Sandy, UT (US); Tony Farnsworth Adams, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 119 days.

(21) Appl. No.: 14/326,036

(22) Filed: Jul. 8, 2014

(65) Prior Publication Data

US 2016/0008517 A1 Jan. 14, 2016

(51) Int. Cl.
*A61L 29/16* (2006.01)
*A61L 29/08* (2006.01)
*A61M 25/00* (2006.01)

(52) U.S. Cl.
CPC ............ *A61L 29/16* (2013.01); *A61L 29/085* (2013.01); *A61L 2300/404* (2013.01); *A61L 2300/606* (2013.01); *A61M 2025/006* (2013.01); *A61M 2025/0046* (2013.01); *A61M 2025/0056* (2013.01)

(58) Field of Classification Search
None
See application file for complete search history.

(56) References Cited

U.S. PATENT DOCUMENTS

| | | | |
|---|---|---|---|
| 3,223,629 A | 12/1965 | Loeffler |
| 3,598,127 A | 8/1971 | Wepsic |
| 3,695,921 A | 10/1972 | Shepherd |
| 3,986,508 A | 10/1976 | Barrington |
| 4,170,996 A | 10/1979 | Wu |
| 4,280,500 A | 7/1981 | Ono |
| 4,339,336 A | 7/1982 | Hammond et al. |
| 4,387,879 A | 6/1983 | Tauschinski |
| 4,449,693 A | 5/1984 | Gereg |
| 4,512,766 A | 4/1985 | Vailancourt |
| 4,584,192 A | 4/1986 | Dell et al. |
| 4,603,152 A | 7/1986 | Laurin et al. |
| 4,610,674 A | 9/1986 | Suzuki |
| 4,629,743 A | 12/1986 | Hong |
| 4,629,746 A | 12/1986 | Michl et al. |
| 4,642,126 A | 2/1987 | Zador et al. |
| 4,676,782 A | 6/1987 | Yamamoto et al. |
| 4,677,143 A | 6/1987 | Laurin et al. |
| 4,716,032 A | 12/1987 | Westfall et al. |
| 4,723,948 A | 2/1988 | Clark |
| 4,781,703 A | 11/1988 | Walker |
| 4,798,594 A | 1/1989 | Hillstead |
| 4,838,873 A | 6/1989 | Landskron |
| 4,874,377 A | 10/1989 | Newgard |
| 4,880,414 A | 11/1989 | Whipple |
| 4,895,566 A | 1/1990 | Lee |
| 4,897,427 A | 1/1990 | Barnavon et al. |
| 4,915,934 A | 4/1990 | Tomlinson |
| 4,925,668 A | 5/1990 | Khan et al. |
| 4,933,178 A | 6/1990 | Capelli |
| 4,935,010 A | 6/1990 | Cox |
| 4,950,257 A | 8/1990 | Hibbs |
| 4,955,890 A | 9/1990 | Yamamoto et al. |
| 4,985,399 A | 1/1991 | Matsuda et al. |
| 5,019,096 A | 5/1991 | Fox, Jr. et al. |
| 5,023,082 A | 6/1991 | Friedman et al. |
| 5,041,097 A | 8/1991 | Johnson |
| 5,053,014 A | 10/1991 | Van Heugten |
| 5,064,416 A | 11/1991 | Newgard |
| 5,077,352 A | 12/1991 | Elton |
| 5,078,703 A | 1/1992 | Bryant |
| 5,098,410 A | 3/1992 | Kerby |
| 5,108,374 A | 4/1992 | Lemieux |
| 5,154,703 A | 10/1992 | Bonaldo |
| 5,156,596 A | 10/1992 | Balbierz |
| 5,217,493 A | 6/1993 | Raad et al. |
| 5,234,410 A | 8/1993 | Graham |
| 5,242,425 A | 9/1993 | White |

(Continued)

FOREIGN PATENT DOCUMENTS

| | | |
|---|---|---|
| CA | 1 331 333 | 8/1994 |
| CA | 2133053 A1 | 3/1995 |

(Continued)

OTHER PUBLICATIONS

"ComfortCoat Hydrophilic Coating," DSM in Medical, http://www.dsm.com/en_US/medical/public/home/pages/product-coating-comfortcoat.jsp, Updated Jan. 11, 2013, Printed Apr. 22, 2013.
"Lubricent—Lubricious Hydrophillic Coatings for Medical Devices," Harland Medical Systems, http://www.harlandmedical.com/index.php/materials/lubricent.html, pp. 1-2, Printed Apr. 22, 2013.
"UV & EB Cure," Xiper Innovations, Inc., http://xiperinnovations.com/uv_eb_cure, Printed Apr. 22, 2013.
Cabot Corporation, "Using Silicas and Aluminas in Coatings,", www.cabot-corp.com/Silicas-And-Aluminas/Coatings, downloaded from the internet on Apr. 26, 2011.
Gama Healthcare, Clinell Alcoholic 2% Chlorhexidine, http://www.gamahealthcare.com/clinellaca2c.html, pp. 1-3, Nov. 7, 2008.

(Continued)

*Primary Examiner* — Sue X Liu
*Assistant Examiner* — Erin E Hirt
(74) *Attorney, Agent, or Firm* — Kirton & McConkie; Craig Metcalf; Kevin Stinger

(57) ABSTRACT

A vascular access device includes an antimicrobial coating that provides kink resistance to a catheter. The antimicrobial coating can extend along a length of the catheter to provide antimicrobial protection when the catheter is inserted into the patient's vasculature. The antimicrobial coating can also increase the effective diameter of the catheter to minimize the likelihood that the catheter will become kinked.

19 Claims, 7 Drawing Sheets

(56) References Cited

U.S. PATENT DOCUMENTS

| | | |
|---|---|---|
| 5,290,246 A | 3/1994 | Yamamoto |
| 5,295,969 A | 3/1994 | Fischell |
| 5,350,363 A | 9/1994 | Goode |
| 5,352,205 A | 10/1994 | Dales |
| 5,357,636 A | 10/1994 | Dresdner, Jr. et al. |
| 5,366,505 A | 11/1994 | Farber |
| 5,405,323 A | 4/1995 | Rogers |
| 5,405,338 A | 4/1995 | Kranys |
| 5,456,948 A | 10/1995 | Mathisen et al. |
| 5,512,199 A | 4/1996 | Khan et al. |
| 5,520,666 A | 5/1996 | Choudhury |
| 5,536,258 A | 7/1996 | Folden |
| 5,540,661 A | 7/1996 | Tomisaka et al. |
| 5,547,662 A | 8/1996 | Khan et al. |
| 5,549,577 A | 8/1996 | Siegel |
| 5,575,769 A | 11/1996 | Vaillancourt |
| 5,616,338 A | 4/1997 | Fox, Jr. et al. |
| 5,629,006 A | 5/1997 | Hoang et al. |
| 5,638,812 A | 6/1997 | Turner |
| 5,651,772 A | 7/1997 | Arnett |
| 5,653,695 A | 8/1997 | Hopkins et al. |
| 5,658,253 A | 8/1997 | Piontek |
| 5,688,747 A | 11/1997 | Khan |
| 5,697,915 A | 12/1997 | Lynn |
| 5,698,229 A | 12/1997 | Ohsumi et al. |
| 5,712,229 A | 1/1998 | Hopkins et al. |
| 5,716,406 A | 2/1998 | Farber |
| 5,763,412 A | 6/1998 | Khan et al. |
| 5,773,487 A | 6/1998 | Sokol |
| 5,806,831 A | 9/1998 | Paradis |
| 5,810,768 A | 9/1998 | Lopez |
| 5,827,239 A | 10/1998 | Dillon |
| 5,830,196 A * | 11/1998 | Hicks ............... A61M 25/0021 604/284 |
| 5,830,401 A | 11/1998 | Prichard |
| 5,861,440 A | 1/1999 | Gohla et al. |
| 5,911,710 A | 6/1999 | Barry |
| 5,944,712 A | 8/1999 | Frassica |
| 5,954,698 A | 9/1999 | Pike |
| 5,957,898 A | 9/1999 | Jepson |
| 6,046,143 A | 4/2000 | Khan et al. |
| 6,051,609 A | 4/2000 | Yu et al. |
| 6,068,622 A | 5/2000 | Sater |
| 6,074,379 A | 6/2000 | Prichard |
| 6,102,890 A | 8/2000 | Stivland |
| 6,117,108 A | 9/2000 | Woehr |
| 6,120,784 A | 9/2000 | Snyder, Jr. |
| 6,127,320 A | 10/2000 | van Ooij et al. |
| 6,171,287 B1 | 1/2001 | Lynn |
| 6,217,566 B1 | 4/2001 | Ju |
| 6,242,526 B1 | 6/2001 | Siddiqui et al. |
| 6,245,098 B1 | 6/2001 | Feeser |
| 6,248,811 B1 | 6/2001 | Ottersbach et al. |
| 6,273,404 B1 | 8/2001 | Holman |
| 6,326,417 B1 | 12/2001 | Jia |
| 6,337,357 B1 | 1/2002 | Fukunishi et al. |
| 6,344,218 B1 | 2/2002 | Dodd et al. |
| 6,353,041 B1 | 3/2002 | Qian |
| 6,387,075 B1 | 5/2002 | Stivland |
| 6,413,539 B1 | 7/2002 | Shalaby |
| 6,426,373 B1 | 7/2002 | Stange |
| 6,475,434 B1 | 11/2002 | Darouiche |
| 6,488,942 B1 | 12/2002 | Ingemann |
| 6,492,445 B2 | 12/2002 | Siddiqui et al. |
| 6,503,353 B1 | 1/2003 | Peterson |
| 6,511,462 B1 | 1/2003 | Itou |
| 6,544,214 B1 | 4/2003 | Utterberg |
| 6,575,958 B1 | 6/2003 | Happ |
| 6,575,960 B2 | 6/2003 | Becker |
| 6,576,633 B1 | 6/2003 | Young et al. |
| 6,579,539 B2 | 6/2003 | Lawson et al. |
| 6,595,981 B2 | 7/2003 | Huet |
| 6,663,614 B1 | 12/2003 | Carter |
| 6,719,991 B2 | 4/2004 | Darouiche et al. |
| 6,723,350 B2 | 4/2004 | Burrell et al. |
| 6,740,063 B2 | 5/2004 | Lynn |
| 6,808,161 B1 | 10/2004 | Hishikawa |
| 6,843,784 B2 | 1/2005 | Modak et al. |
| 6,846,846 B2 | 1/2005 | Modak et al. |
| 6,861,060 B1 | 3/2005 | Luriya et al. |
| 6,887,270 B2 | 5/2005 | Miller et al. |
| 6,893,456 B2 | 5/2005 | Lumauig |
| 6,896,889 B2 | 5/2005 | Chevalier et al. |
| 7,008,404 B2 | 3/2006 | Nakajima |
| 7,074,839 B2 | 7/2006 | Fansler et al. |
| 7,098,256 B2 | 8/2006 | Ong et al. |
| 7,179,849 B2 | 2/2007 | Terry |
| 7,198,800 B1 | 4/2007 | Ko |
| 7,232,540 B2 | 6/2007 | Gould et al. |
| 7,261,925 B2 | 8/2007 | Nesbitt |
| 7,268,165 B2 | 9/2007 | Greten et al. |
| 7,374,798 B2 | 5/2008 | Choo et al. |
| 7,396,346 B2 | 7/2008 | Nakajima |
| 7,407,707 B2 | 8/2008 | Gould et al. |
| 7,462,401 B2 | 12/2008 | Halfyard et al. |
| 7,470,254 B2 | 12/2008 | Basta |
| 7,494,339 B2 | 2/2009 | Dias et al. |
| 7,498,367 B2 | 3/2009 | Qian |
| 7,514,477 B2 | 4/2009 | Klare et al. |
| 7,608,082 B2 | 10/2009 | Cuevas |
| 7,704,935 B1 | 4/2010 | Davis et al. |
| 7,736,339 B2 | 6/2010 | Woehr |
| 7,816,434 B2 | 10/2010 | Hackbarth et al. |
| 7,871,649 B2 | 1/2011 | Modak et al. |
| 7,981,475 B2 | 7/2011 | Takahashi |
| 8,034,454 B2 | 10/2011 | Terry |
| 8,034,455 B2 | 10/2011 | Wang et al. |
| 8,067,402 B2 | 11/2011 | Whiteford et al. |
| 8,133,423 B2 | 3/2012 | Tang |
| 8,227,050 B1 | 7/2012 | O'Neil |
| 8,231,602 B2 | 7/2012 | Anderson |
| 8,263,102 B2 | 9/2012 | Labrecque et al. |
| 8,268,381 B2 | 9/2012 | Whiteford et al. |
| 8,343,523 B2 | 1/2013 | Toreki et al. |
| 8,343,525 B2 | 1/2013 | Davis et al. |
| 8,357,119 B2 | 1/2013 | Stout |
| 8,388,583 B2 | 3/2013 | Stout et al. |
| 8,414,547 B2 | 4/2013 | DiFiore et al. |
| 8,512,294 B2 | 8/2013 | Harding |
| 8,622,995 B2 | 1/2014 | Ziebol et al. |
| 8,622,996 B2 | 1/2014 | Ziebol et al. |
| 8,728,030 B2 | 5/2014 | Woehr |
| 8,840,927 B2 | 9/2014 | Ditizio |
| 9,138,252 B2 | 9/2015 | Bierman |
| 2001/0010016 A1 | 7/2001 | Modak et al. |
| 2001/0016589 A1 | 8/2001 | Modak et al. |
| 2001/0032006 A1 | 10/2001 | Griffin, III et al. |
| 2001/0049519 A1 | 12/2001 | Holman |
| 2001/0053895 A1 | 12/2001 | Vaillancourt |
| 2001/0056133 A1 | 12/2001 | Montgomery et al. |
| 2002/0009436 A1 | 1/2002 | Doyle et al. |
| 2002/0022660 A1 | 2/2002 | Jampani et al. |
| 2002/0028751 A1 | 3/2002 | Lokkesmoe et al. |
| 2002/0037260 A1 | 3/2002 | Budny et al. |
| 2002/0040092 A1 | 4/2002 | Siddiqui et al. |
| 2002/0064858 A1 | 5/2002 | Yacoby-Zeevi |
| 2002/0091424 A1 | 7/2002 | Biel |
| 2002/0119111 A1 | 8/2002 | Kilgour et al. |
| 2002/0133124 A1 | 9/2002 | Leinsing et al. |
| 2002/0144705 A1 | 10/2002 | Brattesani et al. |
| 2003/0060804 A1 | 3/2003 | Vaillancourt |
| 2003/0068667 A1* | 4/2003 | Olson ............... C12M 23/12 435/34 |
| 2003/0072781 A1 | 4/2003 | Pelerin |
| 2003/0105143 A1 | 6/2003 | Ammendola et al. |
| 2003/0119932 A1 | 6/2003 | Al-Akhdar et al. |
| 2003/0134783 A1 | 7/2003 | Harshey et al. |
| 2003/0144362 A1 | 7/2003 | Utterberg |
| 2003/0147932 A1 | 8/2003 | Nun et al. |
| 2003/0162839 A1 | 8/2003 | Symington et al. |
| 2003/0170308 A1 | 9/2003 | Cleary et al. |
| 2003/0176848 A1 | 9/2003 | Gibson et al. |
| 2003/0206875 A1 | 11/2003 | Budny et al. |
| 2003/0215433 A1 | 11/2003 | Kokai-Kun et al. |

(56) References Cited

U.S. PATENT DOCUMENTS

| | | |
|---|---|---|
| 2003/0224032 A1 | 12/2003 | Read et al. |
| 2004/0014864 A1 | 1/2004 | Milic et al. |
| 2004/0039349 A1 | 2/2004 | Modak et al. |
| 2004/0058829 A1 | 3/2004 | Hei et al. |
| 2004/0062592 A1 | 4/2004 | Shekalim |
| 2004/0109852 A1 | 6/2004 | Xu |
| 2004/0115477 A1 | 6/2004 | Nesbitt |
| 2004/0132164 A1 | 7/2004 | Doyle et al. |
| 2004/0180829 A1 | 9/2004 | Bassler et al. |
| 2004/0185296 A1 | 9/2004 | Mazzanti |
| 2004/0230162 A1 | 11/2004 | Tan |
| 2004/0234475 A1 | 11/2004 | Lannibois-Drean et al. |
| 2005/0008671 A1 | 1/2005 | Van Antwerp |
| 2005/0048005 A1 | 3/2005 | Stockel |
| 2005/0048124 A1 | 3/2005 | Sarangapani |
| 2005/0059731 A1 | 3/2005 | Albrecht et al. |
| 2005/0080158 A1 | 4/2005 | Ong et al. |
| 2005/0100580 A1 | 5/2005 | Osborne et al. |
| 2005/0118239 A1 | 6/2005 | Sabesan |
| 2005/0124970 A1 | 6/2005 | Kunin |
| 2005/0131356 A1 | 6/2005 | Ash et al. |
| 2005/0143286 A1 | 6/2005 | Singh et al. |
| 2005/0158253 A1 | 7/2005 | Budny et al. |
| 2005/0176905 A1 | 8/2005 | Moon et al. |
| 2005/0209581 A1 | 9/2005 | Butts |
| 2005/0209583 A1 | 9/2005 | Powers |
| 2005/0233950 A1 | 10/2005 | Madhyastha |
| 2005/0265931 A1 | 12/2005 | Qian |
| 2006/0024372 A1 | 2/2006 | Utterberg et al. |
| 2006/0051385 A1 | 3/2006 | Scholz |
| 2006/0163515 A1 | 7/2006 | Ruschke |
| 2006/0165751 A1 | 7/2006 | Chudzik et al. |
| 2006/0165903 A1 | 7/2006 | Mazzanti |
| 2006/0177477 A1 | 8/2006 | Ash |
| 2006/0239954 A1 | 10/2006 | Sancho |
| 2006/0258780 A1 | 11/2006 | Chaussade et al. |
| 2006/0281663 A1 | 12/2006 | Asmus |
| 2007/0000407 A1 | 1/2007 | Leong |
| 2007/0083157 A1 | 4/2007 | Belley |
| 2007/0083162 A1 | 4/2007 | O'Reagan |
| 2007/0112112 A1 | 5/2007 | Kerschner et al. |
| 2007/0112146 A1 | 5/2007 | Falk et al. |
| 2007/0141524 A1 | 6/2007 | Brennan et al. |
| 2007/0160547 A1 | 7/2007 | Duffy et al. |
| 2007/0166344 A1 | 7/2007 | Qu et al. |
| 2007/0202177 A1 | 8/2007 | Hoang |
| 2007/0203574 A1 | 8/2007 | McGrath et al. |
| 2007/0225179 A1 | 9/2007 | Schutz et al. |
| 2007/0275101 A1 | 11/2007 | Lu et al. |
| 2007/0281198 A1 | 12/2007 | Lousenberg |
| 2008/0026026 A1 | 1/2008 | Lu et al. |
| 2008/0027410 A1 | 1/2008 | Harding |
| 2008/0051737 A1 | 2/2008 | Paul |
| 2008/0075761 A1 | 3/2008 | Modak et al. |
| 2008/0103487 A1 | 5/2008 | Miyasaka |
| 2008/0161763 A1 | 7/2008 | Harding et al. |
| 2008/0182921 A1 | 7/2008 | Suh et al. |
| 2008/0194707 A1 | 8/2008 | Potter |
| 2009/0012220 A1 | 1/2009 | Yamane et al. |
| 2009/0036768 A1 | 2/2009 | Seehusen et al. |
| 2009/0062766 A1 | 3/2009 | Howlett |
| 2009/0101152 A1 | 4/2009 | Burk et al. |
| 2009/0110844 A1 | 4/2009 | Platzer et al. |
| 2009/0114327 A1 | 5/2009 | Breunig |
| 2009/0117164 A1 | 5/2009 | Toreki et al. |
| 2009/0125118 A1 | 5/2009 | Gong |
| 2009/0157007 A1 | 6/2009 | McKinnon |
| 2009/0162530 A1 | 6/2009 | Nesbitt |
| 2009/0176907 A1 | 7/2009 | Subramanian et al. |
| 2009/0188559 A1 | 7/2009 | Nesbitt |
| 2009/0220739 A1 | 9/2009 | Chougule |
| 2009/0226541 A1 | 9/2009 | Scholz et al. |
| 2009/0281525 A1 | 11/2009 | Harding |
| 2009/0299452 A1 | 12/2009 | Eidenschink |
| 2009/0317435 A1 | 12/2009 | Vandesteeg et al. |
| 2009/0324666 A1 | 12/2009 | Krongauz et al. |
| 2009/0324738 A1* | 12/2009 | Krongauz ............ A61L 29/085 424/618 |
| 2010/0069854 A1 | 3/2010 | Okoh |
| 2010/0106102 A1 | 4/2010 | Ziebol |
| 2010/0135949 A1 | 6/2010 | Ou-Yang |
| 2010/0136209 A1 | 6/2010 | Ou-Yang et al. |
| 2010/0137379 A1 | 6/2010 | Ou-Yang |
| 2010/0137472 A1 | 6/2010 | Ou-Yang |
| 2010/0200017 A1 | 8/2010 | Kerr |
| 2010/0204648 A1 | 8/2010 | Stout et al. |
| 2010/0204675 A1 | 8/2010 | Woehr |
| 2011/0009831 A1 | 1/2011 | Burkholz et al. |
| 2011/0065798 A1 | 3/2011 | Hoang et al. |
| 2011/0146680 A1 | 6/2011 | Conway |
| 2011/0150958 A1 | 6/2011 | Davis et al. |
| 2011/0160663 A1 | 6/2011 | Stout et al. |
| 2011/0218529 A1 | 9/2011 | Garcia |
| 2011/0301553 A1 | 12/2011 | Goral et al. |
| 2011/0319825 A1 | 12/2011 | Goral et al. |
| 2012/0016318 A1 | 1/2012 | Hoang |
| 2012/0083750 A1 | 4/2012 | Sansoucy |
| 2012/0111368 A1 | 5/2012 | Rahimy |
| 2013/0165868 A1 | 6/2013 | Isaacson |
| 2013/0196079 A1 | 8/2013 | Schwalm |
| 2013/0204231 A1 | 8/2013 | Ziebol |
| 2013/0274686 A1 | 10/2013 | Ziebol et al. |
| 2013/0310764 A1 | 11/2013 | Burkholz |
| 2013/0330387 A1 | 12/2013 | Ou-Yang |
| 2016/0008517 A1 | 1/2016 | Burkholz |

FOREIGN PATENT DOCUMENTS

| | | | |
|---|---|---|---|
| CN | 1187598 | 7/1998 | |
| CN | 1526771 A | 9/2004 | |
| CN | 101353545 A | 1/2009 | |
| CN | 102070983 A | 5/2011 | |
| DE | 3913392 C2 | 10/1990 | |
| DE | 4011867 A1 | 10/1991 | |
| EP | 0 036 294 A2 | 9/1981 | |
| EP | 0070087 B1 | 1/1983 | |
| EP | 0227230 A1 | 7/1987 | |
| EP | 0 338 418 A1 | 10/1989 | |
| EP | 0370997 A2 | 5/1990 | |
| EP | 0 396 431 A2 | 11/1990 | |
| EP | 0 414 997 A1 | 3/1991 | |
| EP | 0379271 B1 | 10/1993 | |
| EP | 0778337 A2 | 6/1997 | |
| EP | 0992252 B1 | 4/2000 | |
| EP | 1466645 B1 | 10/2004 | |
| EP | 1679043 B1 | 7/2006 | |
| EP | 2868722 A1 * | 5/2015 | ........ C08F 290/067 |
| JP | 05-277434 | 10/1993 | |
| JP | 07-051651 | 2/1995 | |
| JP | H07-47435 A | 2/1995 | |
| JP | 08-209064 | 8/1996 | |
| JP | H08-311373 A | 11/1996 | |
| JP | 09-151262 | 6/1997 | |
| JP | 09-157548 | 6/1997 | |
| JP | 09157548 A | 6/1997 | |
| JP | H09-176677 A | 7/1997 | |
| JP | 09324135 B2 | 12/1997 | |
| JP | H10-231 A | 1/1998 | |
| JP | H11-322560 A | 11/1999 | |
| JP | 2000-178475 A | 6/2000 | |
| JP | 2000178475 A | 6/2000 | |
| JP | 2000-264803 A | 9/2000 | |
| JP | 2001-072438 A | 3/2001 | |
| JP | 2002-282762 | 10/2002 | |
| JP | 2003-342402 | 12/2003 | |
| JP | 2004-043669 A | 2/2004 | |
| JP | 2005-028209 A | 2/2005 | |
| JP | 2005-515838 A | 6/2005 | |
| JP | 2005-520912 A | 7/2005 | |
| JP | 2007-016096 A | 1/2007 | |
| JP | 2008-533051 A | 8/2008 | |
| JP | 2009544454 A | 12/2009 | |
| JP | 2010174075 A | 8/2010 | |
| JP | 2010-536836 A | 12/2010 | |

(56) References Cited

FOREIGN PATENT DOCUMENTS

| | | |
|---|---|---|
| JP | 2012510559 B2 | 5/2012 |
| JP | 2012-532681 A | 12/2012 |
| KR | 20020066429 A | 8/2002 |
| KR | 20080039460 A | 5/2008 |
| WO | 94/22522 A1 | 10/1994 |
| WO | 95/21648 A1 | 8/1995 |
| WO | 96/16690 A1 | 6/1996 |
| WO | 96/40359 A1 | 12/1996 |
| WO | 98/58690 | 12/1998 |
| WO | 98/58989 | 12/1998 |
| WO | 99/16498 A1 | 4/1999 |
| WO | 99/32168 | 7/1999 |
| WO | 99/34849 A1 | 7/1999 |
| WO | 99/36490 A1 | 7/1999 |
| WO | 99/43971 A1 | 9/1999 |
| WO | 1999/43971 A1 | 9/1999 |
| WO | 00/66189 | 11/2000 |
| WO | 00/74743 A1 | 12/2000 |
| WO | 01/95862 A1 | 12/2001 |
| WO | 2004/071568 A1 | 8/2004 |
| WO | 2004/108091 A2 | 12/2004 |
| WO | 2006/012446 A2 | 2/2006 |
| WO | 2006056482 A1 | 6/2006 |
| WO | 2006074666 A2 | 7/2006 |
| WO | 2006/088288 A1 | 8/2006 |
| WO | 2006/099358 A2 | 9/2006 |
| WO | 2006/099359 A2 | 9/2006 |
| WO | 2006/100442 A1 | 9/2006 |
| WO | 2007/064835 A2 | 6/2007 |
| WO | 2007095576 A2 | 8/2007 |
| WO | 2007/100653 A2 | 9/2007 |
| WO | 2007/100776 A2 | 9/2007 |
| WO | 2008/014438 A2 | 1/2008 |
| WO | 2008/014447 A2 | 1/2008 |
| WO | 2008/031601 A1 | 3/2008 |
| WO | 2005/037340 A2 | 4/2008 |
| WO | 2008/045761 A2 | 4/2008 |
| WO | 2008/052790 A2 | 5/2008 |
| WO | 2008/128896 A2 | 10/2008 |
| WO | 2008/132045 A2 | 11/2008 |
| WO | 2009/012336 A1 | 1/2009 |
| WO | 2009/070227 A1 | 6/2009 |
| WO | 2009/114833 A1 | 9/2009 |
| WO | 2010/034470 A1 | 4/2010 |
| WO | WO2010/093791 | 8/2010 |
| WO | 2011/005951 A2 | 1/2011 |
| WO | 2011/034675 A2 | 3/2011 |
| WO | 2011/048204 A2 | 4/2011 |
| WO | WO2011/118680 | 9/2011 |
| WO | 2012/036916 A1 | 3/2012 |
| WO | 2013/009998 A2 | 1/2013 |
| WO | 2013/134421 A1 | 9/2013 |

OTHER PUBLICATIONS

Sage Products, Inc., Preoperative Skin Preparation for the Surgical Patient, http://www.sageproducts.com/products/skin-prep.cfm, 1 page, Oct. 31, 2008.

Sage Products, Inc., Address Multi-Drug Resistant Organisms on the Skin with Early Preop Prep, http://www.sageproducts.com/products/ssi-prevention.cfm, 1 page, Oct. 31, 2008.

Sage Products, Inc., Preoperative Skin Preparation and Perioperative Oral Care for the Short-Term Ventilated Patient, http://www.sageproducts.com/products/ssi-vap-prevention.cfm, 1 page, Oct. 31, 2008.

Enturia, ChloraPrep, http://www.enturia.com/products/chloraPrep/chloraPrep-product.html, pp. 1-3, Oct. 31, 2008.

McDonnell, G., Russell, A.D. Antiseptics and Disinfectants: Activity, Action, and Resistance. Clinical Microbiology Reviews, (1999) 12(1), pp. 149-179.

* cited by examiner

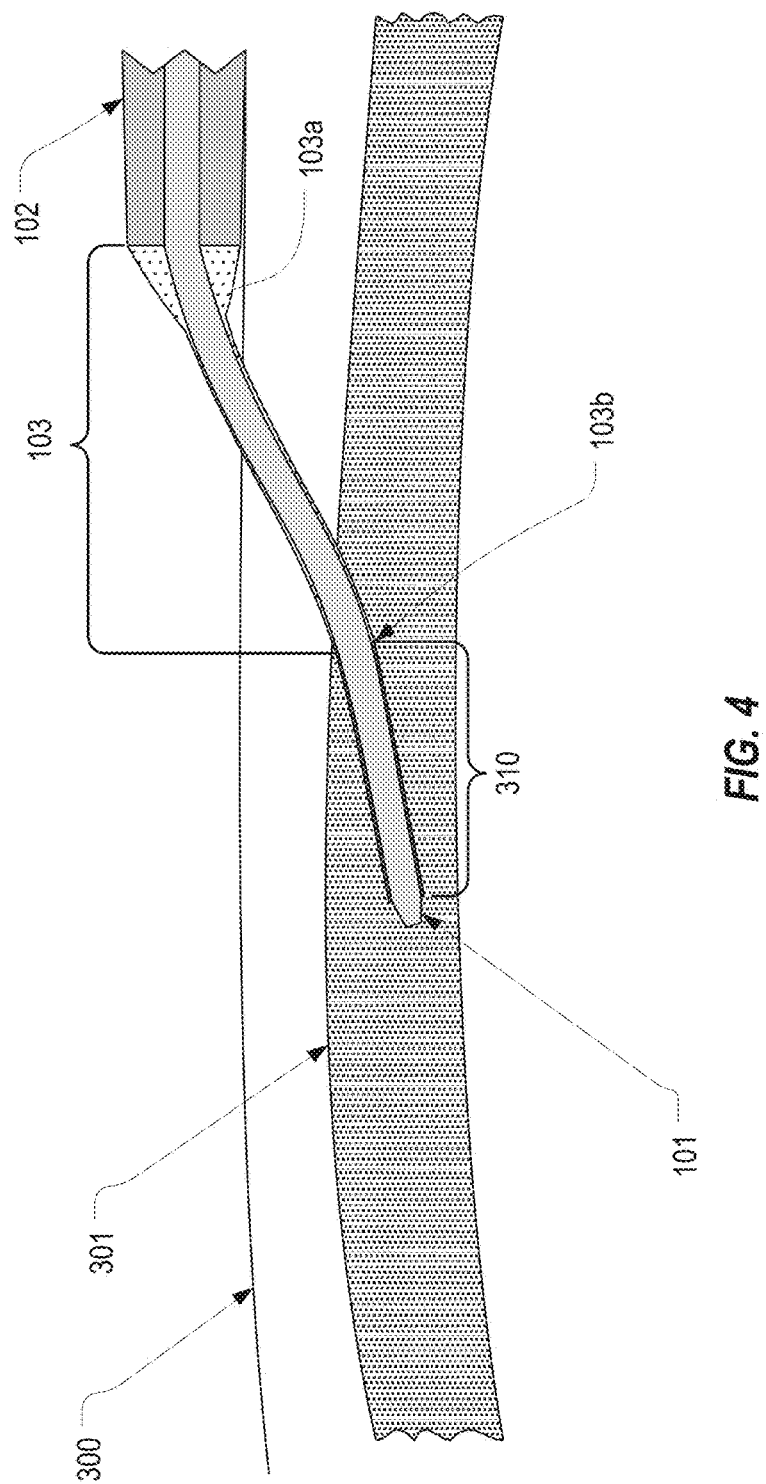

ANTIMICROBIAL COATING FORMING KINK RESISTANT FEATURE ON A VASCULAR ACCESS DEVICE

BACKGROUND OF THE INVENTION

The present invention relates generally to vascular access devices that include an antimicrobial coating. In particular, the present invention is directed to an antimicrobial coating that forms a kink resistant feature on a vascular access device.

It is becoming more common for vascular access devices such as catheters to include an antimicrobial coating to minimize the occurrence of infections caused by the use of the vascular access device. For example, catheters oftentimes include an antimicrobial lubricant that provides lubrication during insertion of the catheter into the patient's vasculature and then provides antimicrobial protection while the catheter is inserted.

One problem that exists with the use of current antimicrobial coatings is the risk of toxicity caused when excess antimicrobial agents enter the bloodstream or are distributed to a confined location. In order to obtain antimicrobial protection for a substantial duration of time (e.g. for the entire time that the catheter is inserted), a significant amount of antimicrobial lubrication must be present on the catheter. With the use of significant amounts of lubrication, there is a risk that too high of a concentration of antimicrobial agents will be distributed.

Another problem that exists with the use of catheters is kinking. For example, when a peripheral intravenous catheter is inserted into the patient's vasculature, it will typically be bent at the point where the catheter exits the catheter adapter (e.g. due to catheter adapter being placed flat on the patient's skin) and possibly where the catheter enters through the patient's skin or vasculature. This bending can oftentimes result in kinks that limit or prevent fluid flow through the catheter.

BRIEF SUMMARY OF THE INVENTION

The present invention extends to vascular access devices that include an antimicrobial coating that provides kink resistance to a catheter. The antimicrobial coating can extend along a length of the catheter to provide antimicrobial protection when the catheter is inserted into the patient's vasculature. The antimicrobial coating can also increase the effective diameter of the catheter to minimize the likelihood that the catheter will become kinked.

In one embodiment, the present invention is implemented as a vascular access device. The vascular access device includes a catheter adapter, a catheter that extends distally from the catheter adapter, and an antimicrobial coating. The antimicrobial coating is applied to at least a portion of the catheter adapter and comprises a base material that releases one or more antimicrobial agents when the antimicrobial coating is inserted within a patient's skin. The base material also provides kink resistance to the catheter.

In some embodiments, the antimicrobial coating can be positioned adjacent the catheter adapter and/or can include an increased diameter portion. In some embodiments, the increased diameter portion is positioned adjacent the catheter adapter.

In some embodiments, the length of the antimicrobial coating can be configured so that the distal end of the antimicrobial coating is positioned near an intimal layer of a vein when the catheter is inserted into the vein. In some embodiments, this length can be between 7 mm and 12 mm.

In some embodiments, the base material can be hydroscopic to enhance the release of the antimicrobial agents when the antimicrobial coating is positioned within the patient's skin. In some embodiments, the base material can be a UV cured acrylate-urethane or a heat-cured polyurethane. In some embodiments, the base material may have a hardness that slightly exceeds a hardness of the catheter.

In some embodiments, the vascular access device can also include an antimicrobial lubricant that is applied to the catheter. In some embodiments, the antimicrobial lubricant can be applied to a portion of the catheter that does not include the antimicrobial coating.

In another embodiment, the present invention is implemented as a vascular access device. The vascular access device includes a catheter adapter, a catheter that extends distally from the catheter adapter, and an antimicrobial coating. The antimicrobial coating extends from the catheter adapter towards a distal end of the catheter and has an increased diameter portion adjacent the catheter adapter.

In another embodiment, the present invention is implemented as a catheter that comprises an antimicrobial coating applied to a portion of the catheter. The antimicrobial coating has a proximal end and a distal end. The proximal end comprises an increased diameter portion. The antimicrobial coating also comprises a base material that releases one or more antimicrobial agents when the antimicrobial coating is positioned within a patient's skin.

This summary is provided to introduce a selection of concepts in a simplified form that are further described below in the Detailed Description. This Summary is not intended to identify key features or essential features of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 4 is a cross-sectional view of a vascular access device with the addition of an antimicrobial lubricant on a distal portion of the catheter.

DETAILED DESCRIPTION OF THE INVENTION

Figure 1:
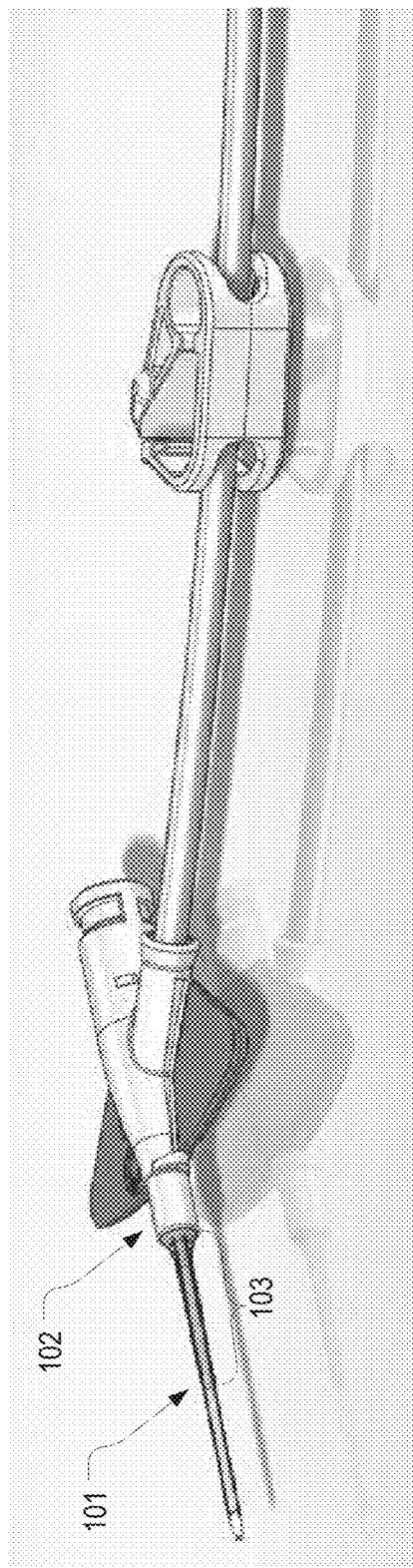
FIG. 1 is a perspective view of a vascular access device that includes an antimicrobial coating that functions as a kink resistant feature on the catheter.

FIG. 1 illustrates an example vascular access device 100 that includes an antimicrobial coating 103 in accordance with one or more embodiments of the invention. Vascular access device 100 includes a catheter adapter 102 and a catheter 101 that extends distally from the catheter adapter. Although vascular access device 100 is shown as including extension tubing, a vascular access device in accordance with the present invention need not include extension tubing. Further, vascular access device 100 is an example of a peripheral intravenous catheter. However, an antimicrobial coating in accordance with the present invention can be applied on other types of catheters including central venous catheters and peripherally inserted central catheters. In short, any device that includes a flexible component that is inserted into the vasculature of a patient can include an antimicrobial coating on the component in accordance with one or more embodiments of the present invention.

The antimicrobial coating may comprise any material that has anti-pathogenic properties which may be applied to the surface of a catheter and that has sufficient rigidity to minimize the likelihood that the catheter will become kinked when it is bent. For example, in some embodiments, the antimicrobial coating can comprise a base material matrix and one or more antimicrobial agents. In some embodiments, the base material matrix can be a UV curable, hydrophilic material that contains an antimicrobial agent with controlled release (elution) characteristics. Alternatively, a base material can be coated with an antimicrobial coating from which an antimicrobial agent will elute when subject to a fluid.

For example, the base material, in some embodiments, can be a water softening UV cure matrix such as UV cured acrylate-urethanes, or heat-cured polyurethanes. Water softening materials can be preferred in many implementations over non-softening materials as such materials become more flexible when inserted into the patient and exposed to fluid. Catheters are oftentimes formed of such water softening materials. Therefore, using an antimicrobial coating that also consists of a water softening material can match the properties of the coating to the catheter to minimize any negative impact the coating may have on the performance of the catheter and on patient comfort. For example, in some embodiments, the hardness of the antimicrobial coating may only slightly exceed that of the catheter. This increased hardness minimizes the likelihood that the catheter will become kinked while minimally affecting the patient's comfort during catheter use because the catheter remains substantially elastic.

Examples of materials that could be used to form the antimicrobial coating of the present invention includes those disclosed in U.S. Pat. No. 8,512,294 titled Vascular Access Device Antimicrobial Materials And Solutions; U.S. patent application Ser. No. 12/397,760 titled Antimicrobial Compositions; U.S. patent application Ser. No. 12/476,997 titled Antimicrobial Coating Compositions; U.S. patent application Ser. No. 12/490,235 titled Systems And Methods For Applying An Antimicrobial Coating To A Medical Device; and U.S. patent application Ser. No. 12/831,880 titled Antimicrobial Coating For Dermally Invasive Devices. Each of these patent documents is incorporated herein by reference.

In one particular embodiment, the antimicrobial agent used to form the antimicrobial coating can be chlorhexidine including chlorhexidine diacetate (CHA) and/or chlorhexidine gluconate (CHG). However, any other antimicrobial agent that will elute from a base material or from a coating on a base material could be used.

Figure 1A:
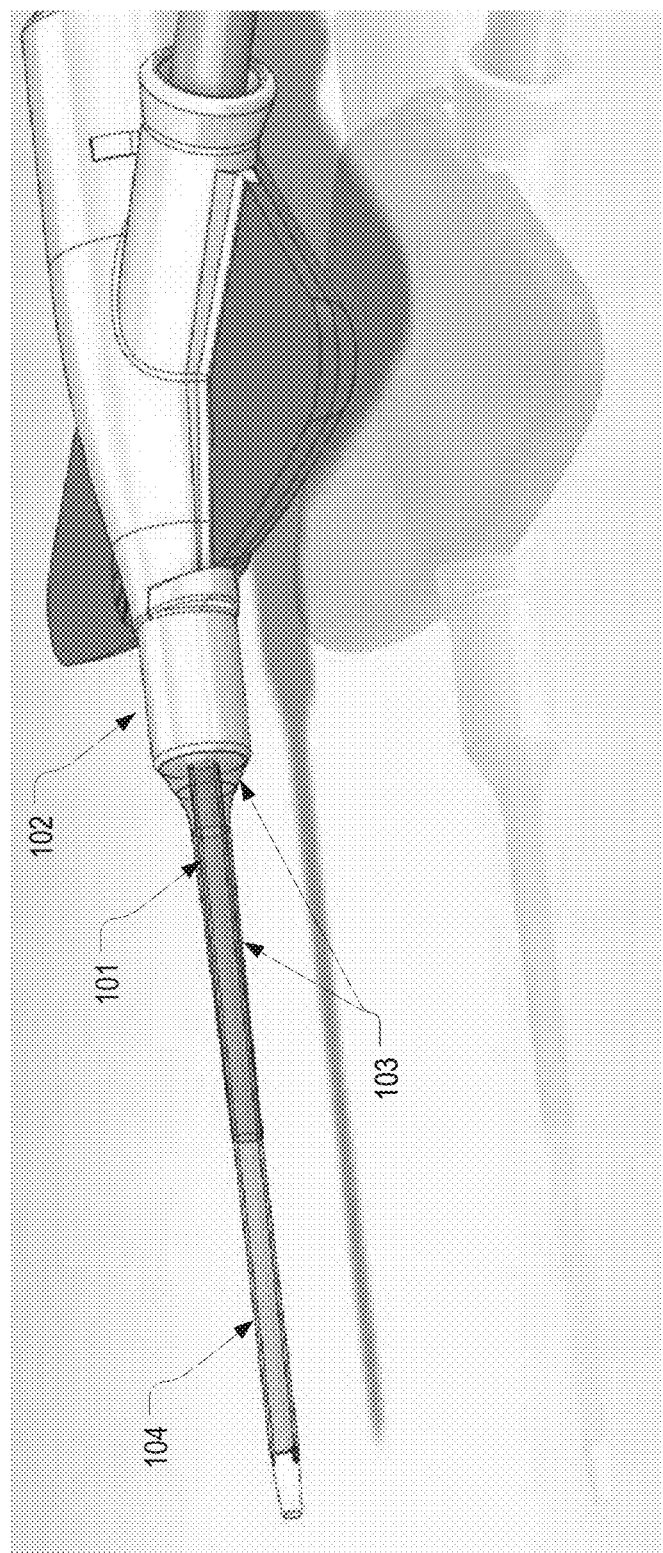
FIG. 1A is a perspective view of the vascular access device of FIG. 1 showing the antimicrobial coating along a length of the catheter.

FIG. 1A illustrates a detailed view of catheter 101 and antimicrobial coating 103. As shown, antimicrobial coating 103 can extend from catheter adapter 102 along a portion of catheter 101. In this example, antimicrobial coating 103 extends along about half the length of catheter 101. However, in some embodiments, antimicrobial coating 103 can extend along a larger or smaller length of catheter 101, including extending to the distal tip.

As best seen in FIG. 1A, the proximal end of antimicrobial coating 103 can have a diameter that increases towards catheter adapter 102. Catheter 101 is most likely to kink as it exits from catheter adapter 102. Therefore, increasing the diameter of antimicrobial coating 103 towards catheter adapter 102 provides additional kink resistance where kinks would otherwise be most likely to occur. In some embodiments, such as is shown in FIG. 1A, the increase in the diameter of antimicrobial coating 103 can be gradually increased to the point that the antimicrobial coating has the same diameter as the nose of catheter adapter 102.

Although in FIGS. 1 and 1A antimicrobial coating 103 is shown as extending only up to catheter adapter 102, in some embodiments, the antimicrobial coating can extend proximally onto a portion of the catheter adapter. Also, in some embodiments, the diameter of the antimicrobial coating at the point where it meets the catheter adapter can be configured to be less than the diameter of the catheter adapter at that point. Further, in some embodiments, rather than having a gradually increasing diameter, the diameter may step up from a smaller diameter to a larger diameter at some distance from the catheter adapter. Accordingly, the present invention encompasses many different types of increases in the diameter of the antimicrobial coating as the coating approaches the catheter adapter.

FIG. 1A also shows that the diameter of antimicrobial coating 103 decreases to a minimal amount at the distal end of the coating. Having a minimal diameter at the distal end of the coating can minimize any discomfort caused to the patient when catheter 101 is inserted.

FIG. 1A also illustrates that, in some embodiments, an antimicrobial lube 104 can be applied to any portion of the catheter that does not include the antimicrobial coating. However, the present invention encompasses embodiments where only an antimicrobial coating is applied to a catheter regardless of whether the antimicrobial coating extends only along a portion of the length of the catheter.

Figure 2:
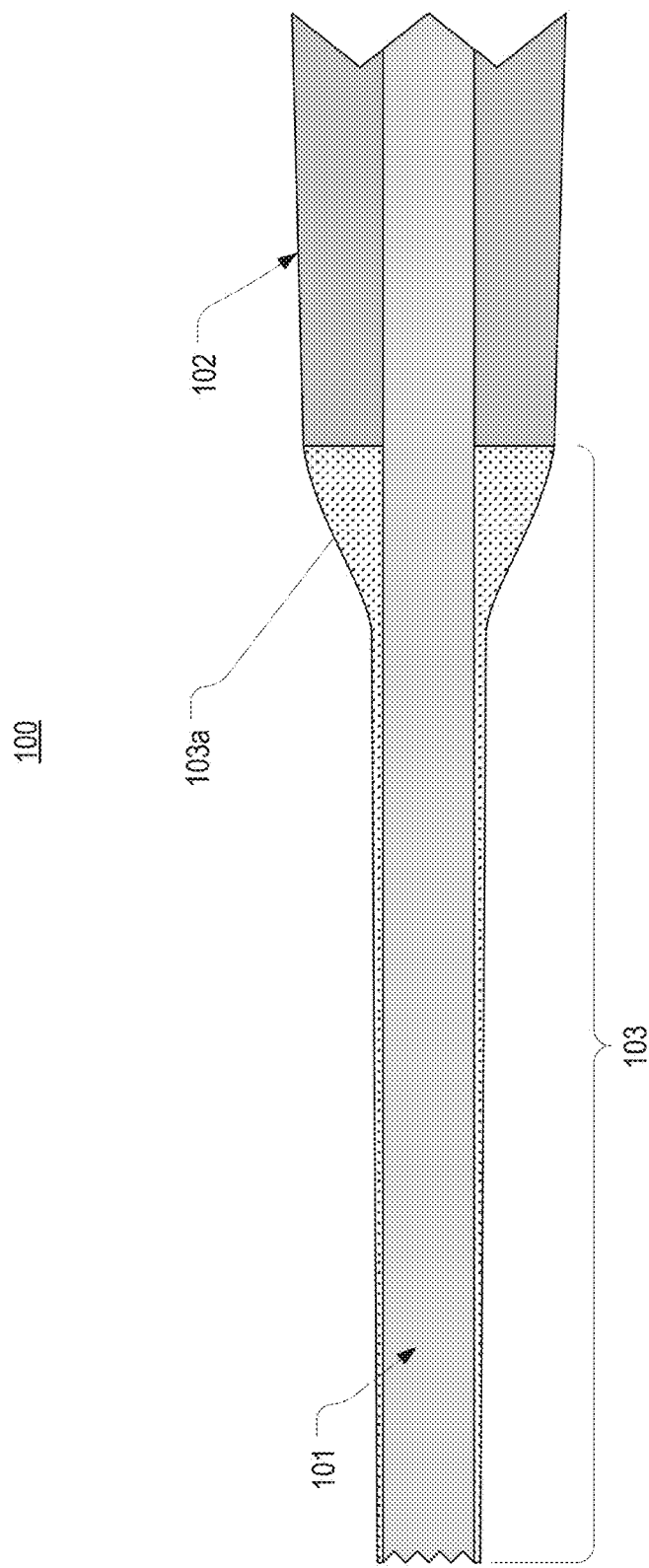
FIG. 2 illustrates a cross-sectional view of a portion of a vascular access device.

FIG. 2 provides a cross-sectional view of vascular access device 100 to better illustrate the increase in the diameter of antimicrobial coating 103. As shown, towards a distal end of antimicrobial coating 103, the diameter of the coating is minimal. In some embodiments, the diameter at this distal end may be between 10 and 100 microns. Then, as antimicrobial coating 103 approaches catheter adapter 102, the diameter gradually increases to form an increased diameter portion 103a. Increased diameter portion 103a can provide increased kink resistance to the catheter as it exits catheter adapter 102. For example, because of the increased diameter of portion 103a, the catheter will be unlikely to bend sufficiently at the point that it exits catheter adapter 102 to cause a kink. In other words, increased diameter portion 103a will tend to cause catheter 101 to bend more gradually as it exits catheter adapter 102 rather than bending sharply at the exit point. Similarly, the other (smaller diameter) portions of antimicrobial coating 103 can provide additional rigidity to catheter 101 to minimize the likelihood of any sharp bends that may result in kinks.

Figure 3:
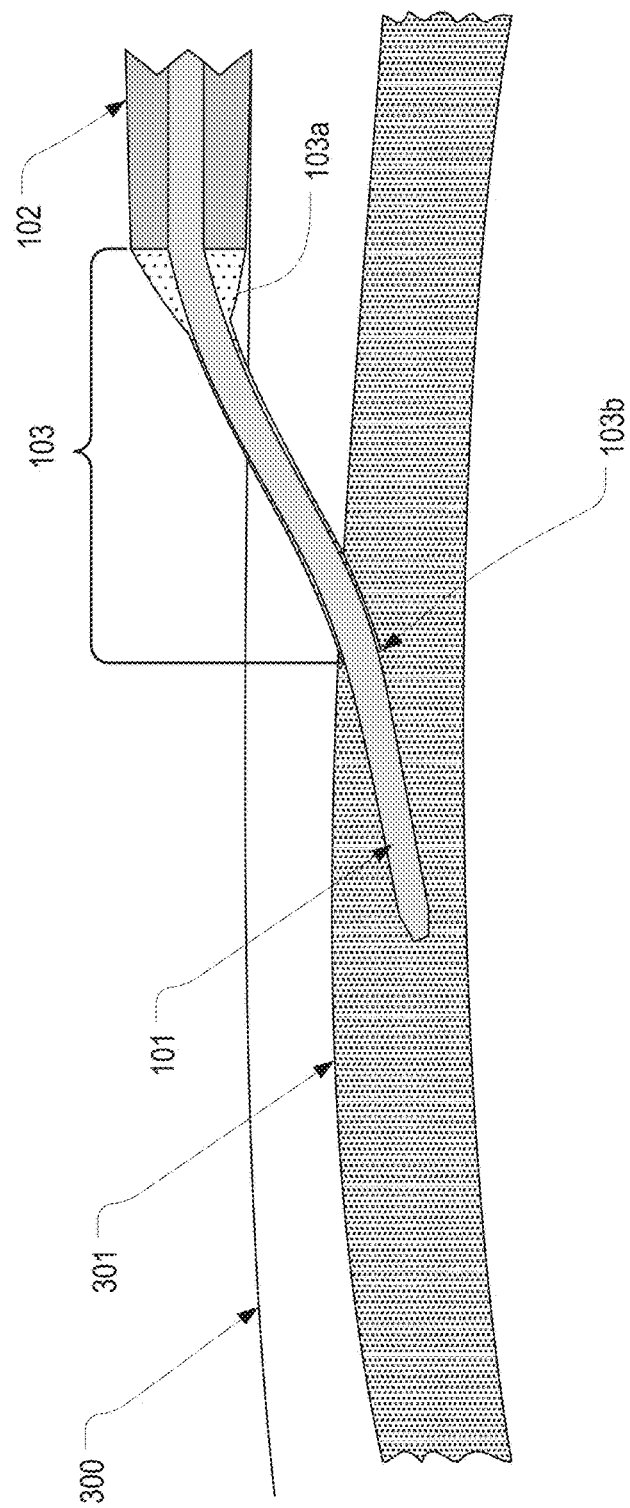
FIG. 3 illustrates a cross-sectional view of the vascular access device of FIG. 2 when it has been inserted into the vasculature of a patient.

FIG. 3 illustrates how antimicrobial coating 103 can provide kink resistance to catheter 101. As shown, catheter adapter 102 is positioned generally flat on the patient's skin 300. Because of this, catheter 101 will be angled downward from the point where it exits catheter adapter 102 to the point where it enters through the patient's skin 300. Antimicrobial coating 103, and more particularly, increased diameter portion 103a causes catheter 101 to bend more gradually between the insertion point and catheter adapter 102 thereby minimizing the likelihood of kinking.

FIG. 3 also illustrates an example where the length of antimicrobial coating 103 is configured so that the coating extends through the dermal layers of skin 300 and into the entrance to vein 301. In this way, antimicrobial agents can be released from antimicrobial coating 103 directly to the dermal layers and at the insertion points into skin 300 and into vein 301. These locations, and particularly the dermal layers, are the primary source of bacteria that may enter vein 301. For this reason, the length of antimicrobial coating 103 can be configured to ensure that antimicrobial agents are targeted to these locations.

Figure 3A:
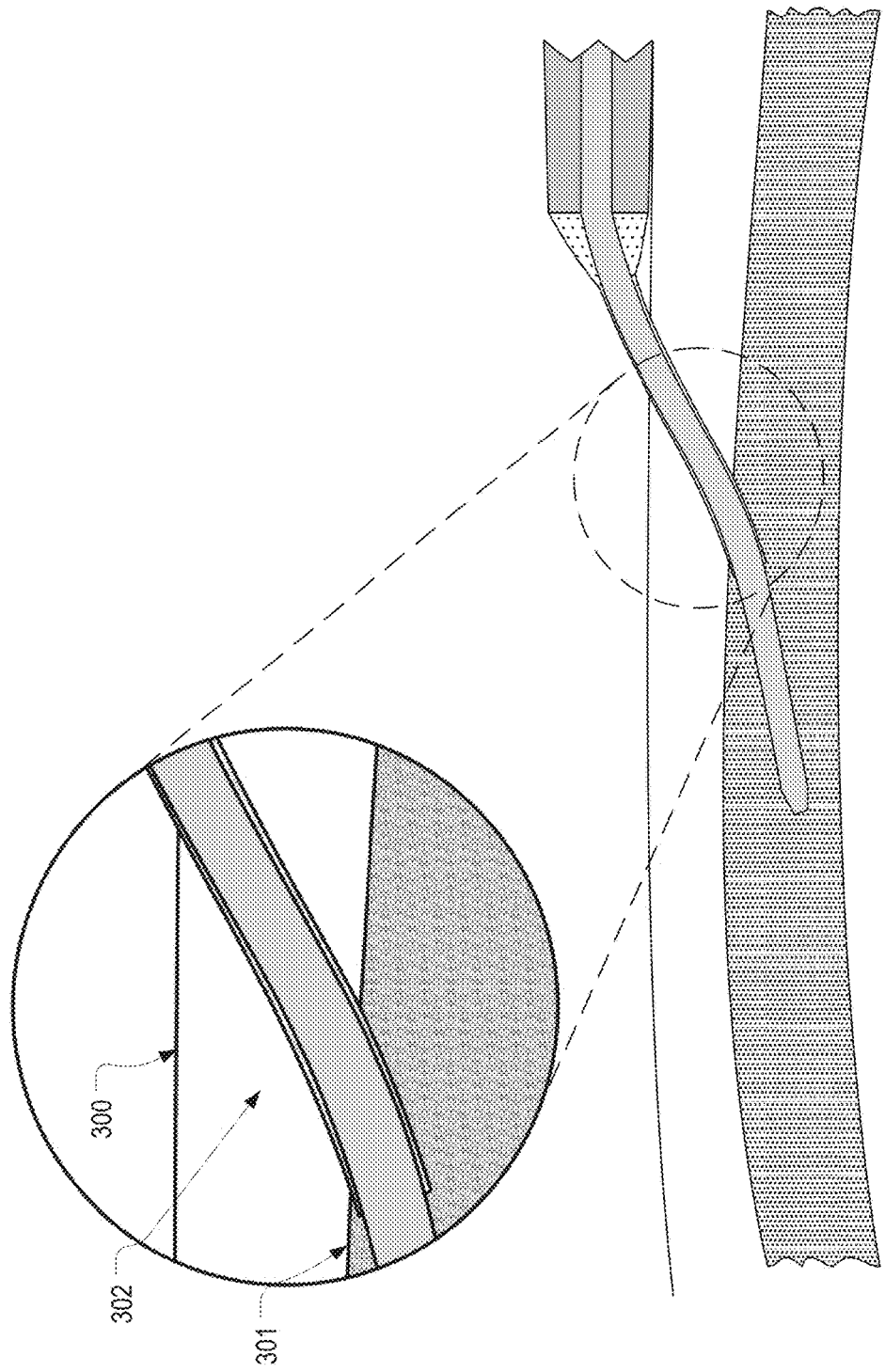
FIG. 3A is a detailed cross-sectional view of the antimicrobial coating in contact with dermal layers of the skin, the primary source of resident bacteria.

FIG. 3A provides a detailed view of a portion of FIG. 3 to illustrate the dermal layers 302 of skin 300 where catheter 101 is inserted. As shown, antimicrobial coating 103 has a sufficient length to ensure that the coating is in contact with the dermal layers. By employing an antimicrobial coating that elutes antimicrobial agents (e.g. a coating that is hydroscopic), the antimicrobial agents can be distributed to the dermal layers (and surrounding areas) in a controlled manner to minimize the possibility of toxicity from the agents.

As addressed above, when an antimicrobial lubricant is used to provide antimicrobial protection to these dermal layers, there is a greater risk of toxicity because it is difficult to ensure that the antimicrobial agents will be localized to the dermal layers and not introduced into the patient's vasculature at toxic levels. In contrast, by employing an antimicrobial coating comprising a base material that elutes antimicrobial agents, the antimicrobial agents can be accurately distributed to the dermal layers 302 and released at a rate that provides long term antimicrobial protection. In other words, antimicrobial coating 103 can limit the total amount of a particular antimicrobial agent that elutes throughout the life of the device, and concentrate the agent in the area of maximum benefit.

To ensure proper positioning of antimicrobial coating 103 when vascular access device 100 is used, antimicrobial coating 103 can be configured with an appropriate length. For example, the depth of tissue between the outer layers of skin and the intimal layers of the vein is commonly between 3 mm and 6 mm. Also, it is typical for 4 mm to 6 mm of the catheter to remain outside of the skin. Therefore, in some embodiments, the length of antimicrobial coating 103 can extend from 7 mm to 12 mm from the catheter adapter to ensure that the distal end of the coating is positioned at least at, if not beyond, the intimal layers of the vein.

Of course, other lengths of antimicrobial coating may be used in other embodiments. In short, the length of the antimicrobial coating can be selected for a particular vascular access device based at least partially on the typical length of the catheter that remains outside of the skin when the particular vascular access device is used. For example, many catheters include a line or other indication that identifies how deep the catheter should be inserted. In some embodiments, the length of antimicrobial coating 103 can be based on the length of the catheter between the catheter adapter and this type of indication. Similarly, the length of the antimicrobial coating may also be based on the distance from the outer layers of the skin and the intimal layers of a vein where the catheter will be inserted (i.e. the length can be based on the intended location where the catheter will typically be inserted).

The antimicrobial coating of the present invention can be particularly beneficial on a vascular access device that is used to draw blood. It is becoming more common to draw blood samples through vascular access devices that have previously been used primarily to inject fluids into the patient's vasculature. When fluids are being injected, there is less concern for kinking because the pressure of the fluid tends to open any kinks that may otherwise occur in the catheter. However, when these same devices are employed to draw blood, kinking is more likely because of the reduced pressures and flow rates used when drawing blood. The antimicrobial coating of the present invention can therefore be particularly beneficial to prevent kinks during blood draw.

FIG. 4 illustrates an alternate embodiment of the vascular access device depicted in FIG. 3. FIG. 4 differs from FIG. 3 in that an antimicrobial lubricant 310 has been applied to the portion of catheter 101 that does not include antimicrobial coating 103. Antimicrobial lubricant 310, in some embodiments, may also extend at least partially over antimicrobial coating 103. Antimicrobial lubricant 310 can provide lubrication to catheter 101 to assist in insertion and can also provide additional antimicrobial protection throughout the insertion site. For example, as catheter 101 is inserted, antimicrobial lubricant 310 can rub off on the dermal layers of the skin to provide immediate and concentrated antimicrobial protection. Then, antimicrobial coating 103, once positioned within the dermal layers, can continue to provide antimicrobial protection in a controlled release and targeted manner. Antimicrobial lubricant 310 can also assist in preventing clots from forming on and in catheter 101, particularly in the distal opening or openings of catheter 101.

Figure 5:
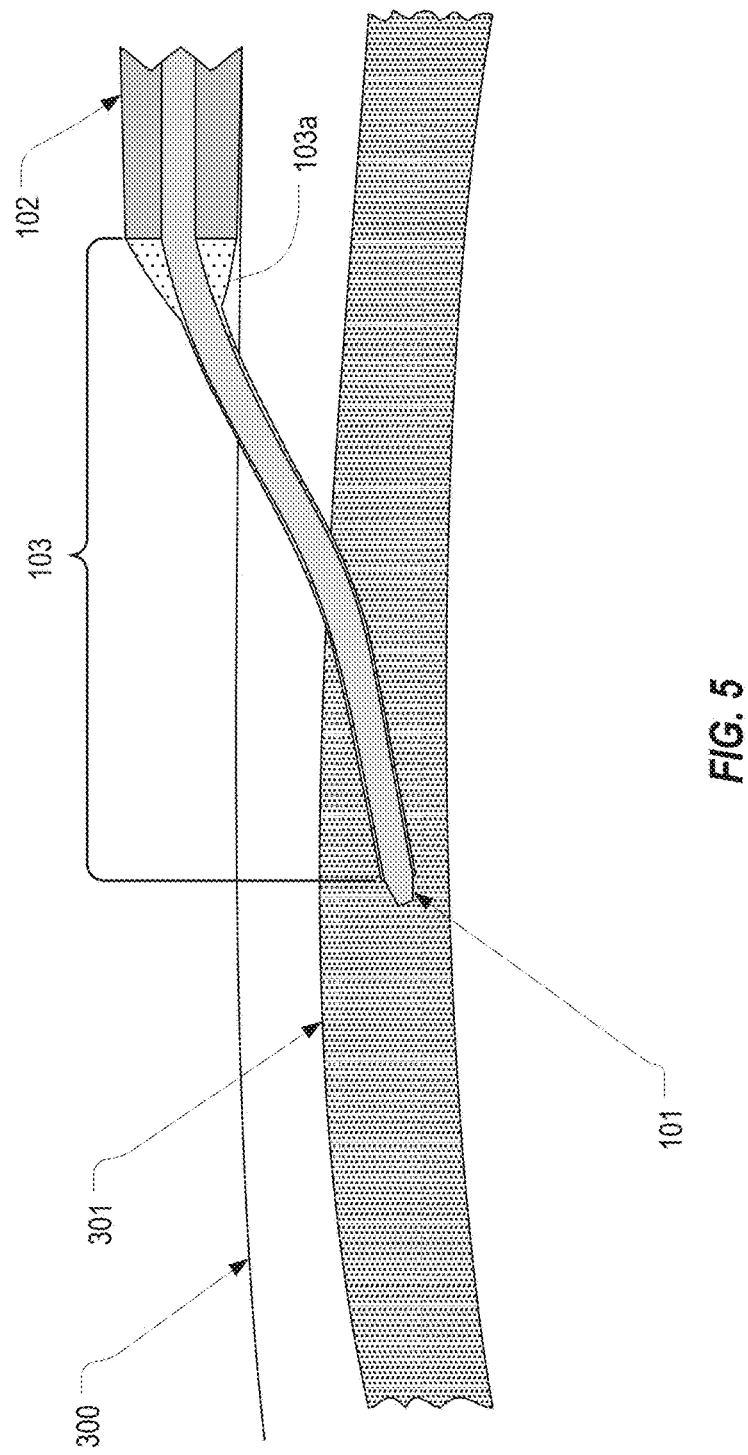
FIG. 5 is a cross-sectional view of a vascular access device when the antimicrobial coating extends along a full length of the catheter.

FIG. 5 illustrates another alternate embodiment of the vascular access device depicted in FIG. 3. FIG. 5 differs from FIG. 3 in that antimicrobial coating 103 extends to the distal end of catheter 101. In such cases, an antimicrobial lubricant, although not depicted, may also be used.

In accordance with one or more embodiments of the invention, an antimicrobial coating can be applied to a vascular access device by dispensing an uncured base material on the catheter adjacent the catheter adapter. This base material can be applied while spinning the catheter slowly (e.g. between 20 and 120 rpm). The catheter can continue to be spun while a die is used to draw the base material over the desired length of the catheter. In some embodiments, a clamshell die may be used. Then, the coating can be cured. In some embodiments, the catheter can continue to be spun while the coating is cured.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A vascular access device comprising:
a catheter adapter;
a catheter that extends distally from the catheter adapter and comprises a material; and
an antimicrobial coating applied to at least a portion of the catheter, the antimicrobial coating comprising a base material that releases one or more antimicrobial agents when the antimicrobial coating is inserted within skin of the patient, wherein the base material is UV cured and has a hardness greater than a hardness of the material of the catheter to provide kink resistance to the catheter, wherein the antimicrobial coating is uniform in thickness along a first portion of the catheter, wherein the antimicrobial coating increases in thickness along a second portion of the catheter adjacent the catheter adapter, wherein when the catheter is inserted into a vein of the patient, the first portion is configured to be positioned at least at an intimal layer of the vein and the second portion is configured to be disposed outside a body of the patient at least proximate the outer layers of the skin.

2. The vascular access device of claim 1, wherein a distal end of the antimicrobial coating is positioned proximal to a distal end of the catheter.

3. The vascular access device of claim 1, wherein the length of the antimicrobial coating is between 7 mm and 12 mm.

4. The vascular access device of claim 1, wherein the base material is hydroscopic.

5. The vascular access device of claim 1, wherein the base material is UV cured acrylate-urethane.

6. The vascular access device of claim 1, wherein a thickness of the antimicrobial coating at a distal end of the antimicrobial coating is between 10 microns and 100 microns.

7. The vascular access device of claim 1, further comprising:
an antimicrobial lubricant applied to the catheter.

8. The vascular access device of claim 7, wherein the antimicrobial lubricant is applied to a portion of the catheter that does not include the antimicrobial coating.

9. A vascular access device comprising:
a catheter adapter;
a catheter that extends distally from the catheter adapter; and
an antimicrobial coating on the catheter, the antimicrobial coating extending from the catheter adapter towards a distal end of the catheter, the antimicrobial coating comprising a base material that releases one or more antimicrobial agents when the antimicrobial coating is inserted within skin of the patient, wherein the base material is cured such that the base material provides increased rigidity to the catheter, the antimicrobial coating having an increased diameter portion adjacent the catheter adapter, wherein the antimicrobial coating increases in thickness from a distal portion of the catheter to a proximal portion of the catheter proximate a distal end of the catheter adapter.

10. The vascular access device of claim 9, wherein the antimicrobial coating has a hardness in excess of a hardness of the catheter.

11. The vascular access device of claim 9, wherein a distal end of the antimicrobial coating is positioned at a length from the catheter adapter that corresponds with a length of the catheter that is intended to exist between an intimal layer of a vein and the catheter adapter when the catheter is inserted into the vein.

12. A vascular access device comprising:
a catheter adapter;
a catheter that extends distally from the catheter adapter; and
an antimicrobial coating applied to a portion of the catheter, the antimicrobial coating having a proximal end and a distal end, the antimicrobial coating comprising a base material that releases one or more antimicrobial agents when the antimicrobial coating is positioned within a patient's skin, wherein the base material is cured such that the base material provides increased rigidity to the catheter, wherein the antimicrobial coating is uniform in thickness along a first portion of the catheter, wherein the antimicrobial coating increases in thickness along a second portion of the catheter adjacent the catheter adapter, wherein an outer diameter of the antimicrobial coating at a proximal end of the second portion equals an outer diameter of a distal end of the catheter adapter.

13. The vascular access device of claim 12, wherein the catheter is positioned within the catheter adapter such that the proximal end of the antimicrobial coating is positioned adjacent the catheter adapter.

14. The vascular access device of claim 1, wherein a length of the second portion is less than 6 mm.

15. The vascular access device of claim 1, wherein the first portion is adjacent to the second portion.

16. The vascular access device of claim 1, wherein the thickness of the antimicrobial coating increases gradually along the second portion of the catheter.

17. The vascular access device of claim 1, wherein the thickness of the antimicrobial coating steps up from a smaller diameter to a larger diameter at some point along the second portion of the catheter.

18. The vascular access device of claim 1, wherein the antimicrobial coating extends beyond a distal end of the catheter adapter onto only a portion of the catheter adapter.

19. The vascular access device of claim 1, wherein a diameter of the antimicrobial coating at a point where the antimicrobial coating meets the catheter adapter is less than a diameter of the catheter adapter at the point.

* * * * *